United States Patent
White

(10) Patent No.: US 11,129,856 B2
(45) Date of Patent: Sep. 28, 2021

(54) METHODS OF TREATING CHRONIC WOUNDS WITH AMNIOTIC FLUID HAVING ELEVATED LEVELS OF TISSUE INHIBITORS OF MATRIX METALLOPROTEINASES

(71) Applicant: Prime Merger Sub, LLC, Birmingham, AL (US)

(72) Inventor: Jeffrey S. White, Chester Springs, PA (US)

(73) Assignee: Prime Merger Sub, LLC, Birmingham, AL (US)

(*) Notice: Subject to any disclaimer, the term of this patent is extended or adjusted under 35 U.S.C. 154(b) by 753 days.

(21) Appl. No.: 15/059,558

(22) Filed: Mar. 3, 2016

(65) Prior Publication Data

US 2016/0256500 A1 Sep. 8, 2016

Related U.S. Application Data

(60) Provisional application No. 62/127,433, filed on Mar. 3, 2015.

(51) Int. Cl.
*A61K 35/50* (2015.01)
*A61K 45/06* (2006.01)
*C12Q 1/37* (2006.01)

(52) U.S. Cl.
CPC .............. *A61K 35/50* (2013.01); *A61K 45/06* (2013.01); *C12Q 1/37* (2013.01); *G01N 2333/96494* (2013.01)

(58) Field of Classification Search
CPC ...................................................... A61K 35/50
See application file for complete search history.

(56) References Cited

PUBLICATIONS

Werber et al. The Journal of Foot & Ankle Surgery 52 615-621 (Year: 2013).*
Muller et al. Diabetic Medicine, 25, 419-426. (Year: 2008).*
Lobmann et al. Diabetes Care, vol. 28, No. 2, pp. 461-471. (Year: 2005).*

* cited by examiner

*Primary Examiner* — Amy L Clark
(74) *Attorney, Agent, or Firm* — C. Brandon Browning; Maynard, Cooper & Gale, PC

(57) ABSTRACT

Methods for treating chronic wounds with an amniotic fluid having a therapeutically effective amount of tissue inhibitors of matrix metalloproteinases (TIMPs) are described. The amniotic fluid can be obtained from a female donor during a period of gestation when the concentration of endogenous TIMPs are at or near their maximum level. The methods described herein are particularly useful for promoting wound healing in chronic wounds having elevated protease activity, such as increased amounts or specific activity of matrix metalloproteinases.

14 Claims, No Drawings

METHODS OF TREATING CHRONIC WOUNDS WITH AMNIOTIC FLUID HAVING ELEVATED LEVELS OF TISSUE INHIBITORS OF MATRIX METALLOPROTEINASES

CROSS REFERENCE TO RELATED APPLICATIONS

This application is entitled to priority pursuant to 35 U.S.C. § 119(e) to U.S. Provisional Patent Application No. 62/127,433, filed Mar. 3, 2015, which is herein incorporated by reference in its entirety.

BRIEF SUMMARY OF THE INVENTION

Wound healing is the body's natural response for repairing and regenerating dermal and epidermal tissue. The wound healing process is complex, and is generally categorized into four stages: (1) clotting/hemostasis stage; (2) inflammatory stage; (3) tissue cell proliferation stage; and (4) tissue cell remodeling stage.

In general, a chronic wound is a wound that does not heal in a predictable amount of time and/or in the orderly set of stages for typical wound healing. Chronic wounds may become caught in one or more of the four states of wound healing, such as remaining in the inflammatory stage for too long, thereby preventing the wound healing process from naturally progressing. A chronic wound may also fail to adequately complete one stage of healing before progressing to the next, causing a disruption in the healing process. As another example, epithelialization that occurs during the tissue proliferation stage typically results in the formation of epithelial cells at the edges of the wound, which proliferate over the wound bed to cover it, and continue until the cells formed at the various sides of the wound converge. However, in the case of chronic wounds, this epithelialization process may be ineffective, because the epithelial cells may not rapidly proliferate over the wound bed or respond to this particular stage of the wound healing process at all.

Wounds that do not heal completely within approximately three months are also considered chronic wounds, and in some cases, chronic wounds may never heal. Such non-healing chronic wounds are often resistant to common wound treatment regimens, and many peripheral wounds that do not heal lead to amputation.

Recently, it has been demonstrated that a subset of non-healing chronic wounds are characterized by elevated protease activity (EPA). In particular, members of the family of matrix metalloproteinases (MMPs) and other proteases, such as serine proteases (e.g., plasmin, neutrophil elastase, mast cell chymase, etc.) have been shown to inhibit wound healing when they have high enzymatic activity levels in the wound. Rationalizing that such wounds might respond to a different treatment regimen than other wounds, point-of-care tests to identify wounds characterized by EPA have been developed. However, to the best of the knowledge of the inventors, a treatment to inhibit, or otherwise remove such proteases in EPA wounds for routine use in the clinic has not yet been developed.

Methods and treatments that are typically used to promote healing of chronic wounds and ameliorate symptoms associated with chronic wounds include antibiotics and antibacterials; non-steroidal anti-inflammatory drugs (NSAIDs) and acetaminophen; cleansing, e.g., with sterile water or sterile saline; surgical or mechanical debridement to remove dead tissue, dirt, or other objects that can delay healing and lead to infection; hyperbaric oxygen therapy (HBO) to increase the amount of oxygen flow in the body; and topical chemical treatment. Additionally, collagen wound dressings have been used to treat chronic wounds, because collagen can be a competing substrate for the proteases that are elevated in chronic wounds, and are thus intended to mitigate the effects of the elevated protease activity. However, these methods have some disadvantages in terms of their efficacy.

Accordingly, there exists a need in the art for improved methods and compositions for treating chronic wounds, and particularly chronic wounds having elevated protease activity.

BRIEF SUMMARY OF THE INVENTION

The invention satisfies this need by providing a method of treating chronic wounds using human amniotic fluid comprising a therapeutically effective amount of tissue inhibitors of matrix metalloproteinases, which can inhibit protease activity in the wound and thus facilitate the healing process of otherwise recalcitrant, non-healing chronic wounds.

In one general aspect, the invention relates to a method of treating a chronic wound in a subject comprising applying a human amniotic fluid or a processed human amniotic fluid comprising a therapeutically effective amount of tissue inhibitors of matrix metalloproteinases to the chronic wound, thereby treating the chronic wound.

According to embodiments of the invention, the human amniotic fluid can be obtained from a donor during a period of gestation when natural levels of TIMPs in the amniotic fluid are relatively high, such as between week 28 and week 37 of gestation.

In a preferred embodiment, the chronic wound is characterized as having elevated protease activity. In other preferred embodiments, the chronic wound is an ulcer, e.g., a diabetic foot ulcer, venous leg ulcer, or pressure ulcer.

In another general aspect, the invention relates to a method of treating a chronic wound in a subject, wherein the chronic wound has elevated protease activity, the method comprising:

(1) identifying a chronic wound as having elevated protease activity; and
(2) applying a human amniotic fluid or a processed human amniotic fluid comprising a therapeutically effective amount of tissue inhibitors of matrix metalloproteinases to the chronic wound identified as having elevated protease activity, thereby treating the chronic wound.

In a preferred embodiment, the step of identifying the chronic wound as having elevated protease activity comprises detecting concentration or activity of one or more matrix metalloproteinases (MMPs) in the wound.

In yet another general aspect, the invention relates to a wound dressing comprising a human amniotic fluid or a processed human amniotic fluid comprising a therapeutically effective amount of tissue inhibitors of matrix metalloproteinases. Embodiments of the invention also relate to methods of treating chronic wounds comprising applying a wound dressing of the invention to the chronic wound, and preferably to a chronic wound having elevated protease activity.

Other aspects, features and advantages of the invention will be apparent from the following disclosure, including the detailed description of the invention and its preferred embodiments and the appended claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. In this application, certain terms are used, which shall have the meanings as set in the specification. It must be noted that as used herein and in the appended claims, the singular forms "a," "an," and "the" include plural reference unless the context clearly dictates otherwise.

It is now discovered that human amniotic fluid and processed human amniotic fluid comprising a therapeutically effective amount of tissue inhibitors of matrix metalloproteinases is effective in treating chronic wounds, and particularly chronic wounds characterized as having elevated protease activity.

As used herein, the term "subject" means any animal, and preferably a mammal. Examples of mammals include, but are not limited to, cows, horses, sheep, pigs, cats, dogs, mice, rats, rabbits, guinea pigs, monkeys, humans etc., more preferably a human.

As used herein, the term "donor" refers to a female subject from whom amniotic fluid will be or has been obtained. The donor can be any animal, preferably a mammal, and is most preferably a human.

As used herein, the term "chronic wound" refers to a wound that does not proceed through the normal repair process of wound healing. The normal repair process of wound healing typically includes four stages: (1) clotting/hemostasis stage; (2) inflammatory stage; (3) tissue cell proliferation stage; and (4) tissue cell remodeling stage. Chronic wounds that do not proceed through the normal repair process of wound healing can stall in one or more stages, inefficiently or ineffectively complete one or more stages, skip one or more stages, or never reach one or more stages of the wound healing process. The term "chronic wound" is also intended to encompass wounds that fail to respond to conventional treatments, and wounds that progress to a non-healing chronic condition. Conditions that slow or stop the wound healing process, thus causing wounds to progress to a non-healing chronic condition include, but are not limited to, poor blood supply or low oxygen supply to tissues in and around a wound; infection, e.g., bacterial infections in the wound; a weakened immune system; and tissue swelling. Weakened immune system can be caused by diseases, such as diabetes and cancer, or poor health and nutrition.

The term "chronic wound" also refers to a wound that does not heal completely within three months. However, wounds that do not heal within thirty days and are being treated according to normal treatment procedures are also considered chronic wounds (see, e.g., the 2005 assessment of chronic wound treatment technologies form the Centers for Medicare and Medicaid Services (CMS)).

Non-limiting examples of chronic wounds include ulcers (e.g., diabetic, venous, decubitus (pressure)); non-healing surgical wounds, trauma wounds, burns, and amputation wounds; and infected tissue compromised by a weakened immune system.

As used herein, the term "ulcer" refers to a break in the skin or a mucous membrane evident by a loss of surface tissue, tissue disintegration, necrosis of epithelial tissue, nerve damage, and/or pus. Typical examples of ulcers include skin ulcers, such as venous ulcers, diabetic ulcers (e.g., diabetic foot ulcer), and decubitus (pressure) ulcers. Venous ulcers usually occur in the legs, and are often the result of improper blood flow and/or restriction in blood flow, leading to tissue damage that causes the wound. Decubitus or pressure ulcers, more commonly referred to as bed sores, are caused by ischemia that occurs when pressure on the tissue is greater than the blood pressure in the capillaries at the wound site, thus restricting blood flow into the area. Pressure ulcers most commonly occur in individuals with limited mobility or paralysis, which inhibits the movement of body parts that are subjected to pressure. Diabetic ulcers, such as diabetic foot ulcers, are open sores or wounds that usually develop on the bottom of the foot of diabetes patients.

Trauma wounds can progress to chronic wound status due to infection or involvement of other factors within the wound bed that inhibit proper healing. Chronic wounds can also arise from burn treatment and related skin grafting procedures that do not proceed through the normal repair process of wound healing. In various types of burns, ulcers, and amputation wounds, skin grafting may be required. In certain instances, patients with ischemia or poor vascularity can experience difficulty in the graft "taking," which can stall the healing process and lead to the formation of chronic wounds in and around the grafting area.

Chronic wound formation can also occur in patients where the risk of infection is high due to a weakened immune system, such as tissue impacted by radiation, patients undergoing cancer treatments, patients affected by immune compromised diseases such as HIV/AIDS, etc. In such patients with a weakened immune system, inflammation of a wound can be prolonged, thereby interfering with the wound healing process and increasing the susceptibility of wounds to develop into chronic wounds.

As used herein, the terms "treat," "treating," and "treatment" are all intended to refer to an amelioration or reversal of at least one measurable physical parameter related to a chronic wound, which is not necessarily discernible in the subject. As an illustrative and non-limiting example, the surface area of the chronic wound is a measurable physical parameter that can be determined before and after treatment to evaluate the effect of the treatment on the chronic wound. The terms "treat," "treating," and "treatment" can refer to improving the progression of wound healing, such as increasing the rate of wound healing. In one embodiment, "treat," "treating," and "treatment" refer to a reduction or an alleviation of one more symptoms associated with chronic wounds, such as pus in and around the wound area; bleeding, swelling, or pain in the wound area; trouble moving the area affected by the wound; deepening and/or enlargement of the wound; and dark or black skin around the wound, particularly dark or black skin that is warm to the touch. In another embodiment, "treat," "treating," and "treatment" refer to partial or complete healing of a chronic wound. In yet another embodiment, "treat," "treating," and "treatment" refer to promoting proliferation of the epithelial cells that grow over the wound bed to cover it. And in yet another embodiment, "treat," "treating," and "treatment" refer to restoring the progression of a disturbed wound healing process to the normal stages of the repair process.

"Matrix metalloproteinases" and "MMPs" refer to a family of zinc-dependent endopeptidases. MMPs are produced by inflammatory cells (e.g., neutrophils and macrophages) and wound cells (e.g., epithelial cells, fibroblasts, vascular endothelial cells), and play a role in many biological processes, including cell proliferation, inflammation, and wound healing. MMPs are first produced and released in an inactive form known as the "pro-MMP" form. Inactive pro-MMPs are subsequently activated by proteases that cleave off a portion of the protein. Examples of MMPs include, but are not limited to, MMP-1, MMP-2, MMP-3, MMP-4, MMP-5, MMP-6, MMP-7, MMP-8, and MMP-9. Although the specific natural substrates for each of the MMPs varies, MMPs are generally capable of degrading extracellular matrix proteins, such as collagen, gelatin, proteoglycans, etc.

As used herein, "tissue inhibitor of matrix metalloproteinases" and "TIMPs" refer to a family of protease inhibitors that modulate the activity of matrix metalloproteinases. The human genome encodes four TIMPs: TIMP1, TIMP2, TIMP3, and TIMP4. TIMPs modulate matrix metalloproteinases by inhibiting the activity of activated MMPs, or by blocking the activation of pro-MMPs. According to embodiments of the invention, an amniotic fluid comprising a therapeutically effective amount of TIMPs can affect the activity of MMPs in a wound by inhibiting the activity of activated MMPs, or by blocking the activation of pro-MMPs.

As used herein, "elevated protease activity" and "EPA," when used with reference to a chronic wound, are intended to refer to an increased level of enzymatic activity of certain proteases present within the wound. Examples of proteases that can have elevated activity within a wound include matrix metalloproteinases and serine proteases, such as plasmin, neutrophil elastase, cell chymase, etc. A wound characterized as having an elevated protease activity, or that is referred to as an "EPA wound," is a wound in which the enzymatic activity level of proteases, particularly matrix metalloproteinases, is increased as compared to the activity detected of the same proteases in a wound in which healing is progressing according to the normal repair process. The increased enzymatic activity detected can be the result of an increased concentration or amount of proteases in the wound, or it can be due to increased specific activity of the proteases. For example, increased enzymatic activity of MMPs detected in a wound can result from an increased amount of MMPs present in the wound; an increased amount of MIMPs present in the activated form, rather than the pro-MMP inactive form; and/or an increased amount of MMPs uninhibited by TIMPs, any of which can lead to a higher detectable level of enzymatic activity in the wound.

The term "therapeutically effective amount" is intended to refer to an amount of an active ingredient or component that elicits the desired biological or medicinal response in a subject. As used herein with reference to tissue inhibitors of matrix metalloproteinases (TIMPs), a therapeutically effective amount means an amount of TIMPs that results in treatment of a chronic wound in a subject, including improving the progression of wound healing, reducing or alleviating one or more symptoms associated with chronic wounds, partial or complete healing of the chronic wound, promoting proliferation of epithelial cells that grow over and cover the wound bed, and restoring the progression of a disturbed wound healing process to the normal states of the repair process. One of ordinary skill in the art will recognize that the therapeutically effective amount of TIMPs to be used in the invention can vary with factors, such as the particular subject, (e.g., age, diet, health, etc.), type of chronic wound, severity of the chronic wound, and any underlying complications or conditions in the subject that slow or stop the wound healing process. For example, many chronic wound patients have one or more underlying complications or conditions that can affect the wound healing process and thus subsequent treatment of the wound, such as diabetes, smoking, vascular disease, obesity, auto-immune disease and the like.

The invention provides methods of treating chronic wounds in a subject comprising applying a human amniotic fluid or a processed human amniotic fluid to the chronic wound. According to embodiments of the invention, the amniotic fluid comprises a therapeutically effective amount of tissue inhibitors of matrix metalloproteinases (TIMPs), which can inhibit proteases in the wound that interfere with the wound repair process, thereby facilitating wound healing. Amniotic fluid naturally contains TIMPs, as well as many other regenerative components that are efficacious for wound healing, such as growth factors, stem cells, protease inhibitors, etc. Accordingly, providing a therapeutically effective amount of TIMPs in an amniotic fluid can further enhance healing of chronic wounds as a result of the other components present in the amniotic fluid.

During gestation of an embryo, the body creates a placental sac made of amnion and chorion tissues surrounding the fetus and containing amniotic fluid to both protect and nourish the fetus. A purpose of TIMPs in amniotic fluid is to prevent the amnion and chorion tissues from being prematurely degraded by proteases, as such degradation would cause premature rupture of the placental sac and pre-term birth of the fetus. However, once the pregnancy has reached full term, TIMP levels in the amniotic fluid typically will fall abruptly, which allows for degradation of the amnion and chorion tissues, release of the amniotic fluid, and subsequent birth of the fetus. Thus, TIMP levels in amniotic fluid are typically at their highest during the late pre-term period of pregnancy, which prevents degradation of the amnion and chorion tissues, thus maintaining the integrity of the placental sac.

According to embodiments of the invention, the therapeutically effective amount of TIMPs can be provided by the natural level of TIMPs endogenously present in the amniotic fluid, or the therapeutically effective amount of TIMPs can be provided by supplementing the amniotic fluid with endogenous TIMPs. Supplementing the amniotic fluid collected from the female donor with exogenous TIMPs, e.g., purified TIMPs, can increase the effective concentration of TIMPs in the amniotic fluid and further enhance its effects on wound healing.

In a preferred embodiment, the amniotic fluid is a processed amniotic fluid, more preferably a processed human amniotic fluid. As used herein, the term "processed amniotic fluid" is an amniotic fluid that has been manipulated in some way after being collected from the donor. For example, the amniotic fluid collected from the donor can be concentrated to remove water from the amniotic fluid, thus concentrating many amniotic fluid components, including TIMPs. Concentrating amniotic fluid can increase the concentration of TIMPs and/or other components in the amniotic fluid, thus achieving optimal therapeutic concentrations of TIMPs and other components in the amniotic fluid, which can further enhance wound healing. However, the invention is not limited to processing amniotic fluid by removing water to concentrate TIMPs, and other methods can be used to optimize the concentration of TIMPs in the amniotic fluid. For example, the amniotic fluid can also be processed by exogenously adding one or more components, e.g., TIMPs to the amniotic fluid, thus increasing the concentration of TIMPs.

According to embodiments of the invention, the amniotic fluid can be obtained from a human female donor during gestation at a point when TIMP levels are typically near or at their maximum. As known by one of ordinary skill in the art, the gestation period in human females is divided into three trimesters: the first trimester (weeks one through twelve), the second trimester (weeks thirteen through twenty-seven), and the third trimester (weeks twenty-eight to birth). Gestation in human females is also characterized according to terms, i.e., specific periods of gestation during which birth occurs: pre-term (before 37 weeks of gestation), early term (37 weeks to 38 weeks, 6 days of gestation), full term (39 weeks to 40 weeks, 6 days of gestation), and late term (41 weeks to 41 weeks 6 days of gestation). TIMP levels have been demonstrated to fall rapidly in amniotic fluid at birth. Therefore, in a preferred embodiment, the amniotic fluid is obtained at a point just prior to birth.

According to embodiments of the invention, human amniotic fluid for use in the invention can be obtained from a human female donor. Preferably, the amniotic fluid is obtained at the time of Caesarean section delivery. When the Caesarean section delivery is elective, collection of the amniotic fluid can occur during the late pre-term period of pregnancy, i.e., during weeks 28 to 37 of gestation, and preferably closer to week 37 of gestation, when TIMP levels are typically at or near their maximum. For example, the amniotic fluid can be obtained during week 28, 29, 30, 31, 32, 33, 34, 35, 36, or 37 of gestation.

According to embodiments of the invention, the method of treating a chronic wound can further comprise determining the concentration of TIMPs in the amniotic fluid, thereby verifying that the amniotic fluid has an increased concentration of TIMPs. Any method known in the art in view of the present disclosure can be used to determine the concentration of TIMPs, such as enzyme-linked immunoabsorbent assay (ELISA), Bradford assay, electrophoresis techniques (e.g., SDS-PAGE, Western blot), etc. For example, the concentration of TIMPs can be determined by testing a sample of amniotic fluid obtained by amniocentesis or at the time of the Caesarean section delivery.

The amniotic fluid can be further processed so that it has a relatively high viscosity for ease of application and for remaining in the desired area after the application. For example, the amniotic fluid can be concentrated to remove water by any technique known to those skilled in the art in view of the present disclosure including, but not limited to, dialysis, diffusion techniques, centrifugation, lyophilization, and vacuum filtration. The amniotic fluid can be further treated in order to promote preservation, lengthen shelf life, or improve stability. These treatments include, but are not limited to, sterilization, e.g., gamma-irradiation; cooling, refrigeration, and freezing; and addition of one or more excipients. Examples of excipients that can be included in the amniotic fluid include, but are not limited to, preservatives; cryopreservatives; antimicrobial agents and other substances to prevent the growth of microbes, such as antimicrobial and antiviral agents; thickeners; salts; colorants; and agents that improve the viscosity of the composition.

According to embodiments of the present invention, the amniotic fluid can further comprise a cryoprotectant. Any cryoprotectant suitable for pharmaceutical use known to those skilled in the art in view of the present disclosure can be used including, but not limited to dimethyl sulfoxide (DMSO), sucrose, glycerol, glucose, and any other sugars, e.g., monosaccharides or disaccharides, alcohols and penetrating agents, or combinations thereof.

Preferably, the amniotic fluid is free of particulate matter, such as cellular debris and tissue debris. Particulate matter can be removed from the amniotic fluid by any method known in the art for removing particulate matter from biological samples, including but not limited to filtration and centrifugation. Particulate matter can be removed at any time after the amniotic fluid has been collected from the donor. Preferably, the particulate material is removed prior to any other processing or treatment steps.

For example, using an ultrafiltration approach, a semi-permeable container is filled with raw amniotic fluid, and then a pressure gradient is applied across the semi-permeable membrane using any number of techniques known to those skilled in the art including, but not limited to, a high permeability dialyzer. As another illustrative example, when employing hemodialysis techniques, an electrolyte solution (dialysate) can be applied on one side of a membrane, creating a concentration gradient, which causes water and other non-protein cellular components of the amniotic fluid to flow through the semi-permeable membrane. As yet another illustrative example, rapid ultrafiltration approaches can be used. Rapid ultrafiltration approaches employ a semi-permeable membrane cylindrical container that rotates constantly in order to avoid filter clogging even as a pressure gradient is applied to the contained fluid—either from within the container (pushing), or from the opposite side of the semi-permeable membrane (pulling). The amniotic fluid can also be concentrated by removal of water using any technique known to those of ordinary skill in the art. For example, substantially all of the water can be removed by lyophilization, or the amount of water can simply be reduced by vacuum filtration. Other methods that can be used to process the amniotic fluid are described in U.S. patent application Ser. No. 14/950,186, which is herein incorporated by reference in its entirety.

According to embodiments of the invention, any chronic wound in view of the present disclosure can be treated by the methods described herein. In a preferred embodiment, the chronic wound is identified as having elevated protease activity. Preferred examples of chronic wounds to be treated by the methods of the invention include ulcers, preferably skin ulcers, such as diabetic ulcers (e.g., diabetic foot ulcer), venous ulcers, and pressure ulcers, and particularly preferred examples of chronic wounds are elevated protease activity skin ulcers, such as diabetic ulcers (e.g., diabetic foot ulcer), venous ulcers, and pressure ulcers. Other examples of chronic wounds to be treated by methods of the invention include infected wounds in patients with a compromised immune system; non-healing surgical wounds, trauma wounds, and burn wounds; wounds that have progressed to a non-healing chronic state as a result of poor blood supply or low oxygen supply to tissues in and around a wound, infection, or tissue swelling; and wounds from skin graft failure.

In certain embodiments of the invention, a chronic wound to be treated is a chronic wound having elevated protease activity (EPA), particularly elevated activity of matrix metalloproteinases (MMPs). Particular MMPs that are known to play a role in wound healing and/or inflammation include MMP-1, MMP-2, MMP-8, and MMP-9. When MMPs are present in a wound at too high a level, they begin to degrade proteins that are not their normal substrates, which can result in degradation of proteins that are essential for wound healing, such as extracellular matrix proteins, thus impairing the healing process.

In a preferred embodiment of the invention, the chronic wound to be treated has elevated activity of one or more MMPs, particularly one or more MMPs selected from the group consisting of MMP-1, MMP-2, MMP-8, and MMP-9.

A method of treating a chronic wound according to an embodiment of the invention can further comprise a step of identifying a chronic wound as having elevated protease activity. Any method known in the art in view of the present disclosure can be used to determine if a chronic wound has elevated protease activity. For example, biological samples, such as fluid or swabs, can be taken directly from the wound bed to be tested for elevated protease activity. The biological samples can then be analyzed using in vitro techniques to qualitatively or quantitatively detect or measure the enzymatic activity level or concentration of the proteases of interest. Any method or assay known in the art in view of the present disclosure can be used to detect or measure enzymatic activity or concentration, including, but not limited to, immunochromatographic methods, colorimetric assays, fluorescence-based assays, ELISA, Bradford assay, electrophoresis techniques (e.g., SDS-PAGE, Western blot), etc.

In particular embodiments of the invention, in vitro assays designed to specifically detect MMP activity can be used to analyze the biological samples taken from the wound. The in vitro assays can be used at point of care. Commercially available kits and tests for measuring elevated protease activity in wounds, as well as commercially available kits and tests for specifically measuring MMP activity can also be used with a method of the invention. Such kits and tests can be used according to the manufacturer's instructions.

According to embodiments of the invention, the amniotic fluid can be administered to a chronic wound alone or in combination with one or more active agents. Examples of active agents that can be administered with the amniotic fluid include, but are not limited to, morphogenic proteins, small molecule compounds, pharmaceutical agents, antimicrobial agents, anti-inflammatory agent, agents that prevent scarring and/or adhesions, and analgesics. Administering the amniotic fluid in combination with such an active agent may further enhance the wound healing process by promoting epithelial cell proliferation, decreasing inflammation, reducing or preventing infection, alleviating pain, etc.

The chronic wound can be cleansed prior to application of the amniotic fluid. For example, the wound can be washed with water or a sterile saline solution. The wound can also be treated by surgical or mechanical debridement to remove dead tissue, dirt, or other objects that can delay healing and lead to infection.

According to embodiments of the invention, the amniotic fluid can be applied as a single application to a wound, or it can be applied multiple times, e.g., in 1, 2, 3, 4, 5, 6, 7, 8, 9, or 10 applications, etc. The amniotic fluid can be applied once a day, or multiple times a day. The amniotic fluid can be continually re-applied to the wound for a period of a few days, a few weeks, or a few months, and is preferably reapplied until complete healing of the wound is observed. The optimal number, frequency, and duration of applications of the amniotic fluid will depend upon various factors including the particular type of wound, how long the chronic wound has been persisting, the underlying cause of the chronic wound, etc. One of ordinary skill in the art will be able to determine the frequency and duration of applications of the amniotic fluid in view of the above factors in order to achieve the desired outcome.

The invention also relates to a wound dressing comprising a human amniotic fluid or a processed human amniotic fluid comprising a therapeutically effective amount of tissue inhibitors of matrix metalloproteinases. The term "wound dressing" as used herein refers to a material used for covering or protecting a wound. For example, a wound dressing can be a surgical dressing, a bandage, or any other material suitable for covering or protecting a wound.

According to embodiments of the invention, the wound dressing can be absorbed with the human amniotic fluid. The wound dressing can comprise any amniotic fluid in view of the present disclosure.

The wound dressing can be made of any material suitable for covering a chronic wound. Examples of suitable materials include, but are not limited to, any medical grade polymer or monomer, polyvinyl alcohol (PVA), polytetrafluoroethylene (PTFE), expanded polytetrafluoroethylene (ePTFE), porous polyethylene, porous polypropylenes, etc. Applying an amniotic fluid comprising a therapeutically effective amount of TIMPs absorbed in a wound dressing can further enhance the wound healing process by providing a protective covering to the chronic wound, which can prevent infection, keep the wound clean, etc.

According to embodiments of the invention, the wound dressing or bandage can be used in a method of treating a chronic wound of the invention. The method comprises applying the wound dressing to a chronic wound, thereby treating the chronic wound. Preferably, the chronic wound is a chronic wound having elevated protease activity. Thus, in a preferred embodiment, the method further comprises a step of identifying a chronic wound as a wound having elevated protease activity prior to applying the wound dressing to the chronic wound. A wound dressing according to embodiments of the invention can be used in any of the methods described herein.

Embodiments of the invention also relate to harvesting TIMPs from amniotic fluid obtained from the donor, preferably amniotic fluid obtained from the donor at a point during gestation when the level of TIMPs is at or near the maximum. TIMPs harvested from the amniotic fluid can be purified and formulated into a pharmaceutical composition suitable for application to a chronic wound. TIMPs harvested from the amniotic fluid can also be used to supplement an amniotic fluid prior to application of the amniotic fluid to a chronic wound. TIMPs can be harvested from amniotic fluid by any method known in the art for purifying and isolating proteins from biological mixtures in view of the present disclosure, such as size-exclusion chromatography, ultracentrifugation, affinity chromatography, or other chromatographic separation methods, etc.

In one embodiment of the invention, a method of treating a chronic wound in subject comprises applying a pharmaceutical composition comprising a therapeutically effective amount of TIMPs to the chronic wound, thereby treating the chronic wound. The method can further comprise identifying a chronic wound as having elevated protease activity, such as elevated protease activity of one or more MMPs, e.g., MMP-1, MMP-2, MMP-8, MMP-9, etc. Any chronic wound in view of the present disclosure can be treated by applying a pharmaceutical composition comprising a therapeutically effective amount of TIMPs according to a method of the invention.

Methods of obtaining an amniotic fluid from a donor using the appropriate sterile techniques are well known to those of ordinary skill in the art. One of ordinary skill in the art is also familiar with procedures for safely and humanely obtaining an amniotic fluid from a donor in an aseptic manner. For example, human amniotic fluid can be obtained from a donor who is undergoing an amniocentesis procedure, Caesarean section delivery, or vaginal birth using a specially designed receptacle to collect the fluid. Preferably, the amniotic fluid is obtained from a donor undergoing a Caesarean section delivery, and is more preferably obtained from a donor undergoing a pre-term Caesarean section delivery, i.e., prior to week 37 of gestation. Amniotic fluid obtained from a donor undergoing vaginal birth, or from an amniocentesis procedure can also be used with a method of the invention, however a larger quantity of amniotic fluid can be obtained from a donor undergoing a Caesarean section delivery, and is thus the preferred method for obtaining amniotic fluid. Also, amniotic fluid at the time of vaginal delivery at term typically has lower levels of TIMPs.

According to embodiments of the invention, amniotic fluid used in the invention is procured from a female donor. Informed consent is obtained from the female donor by following guidelines as promulgated by the American Association of Tissue Banks and consistent with guidelines provided by the Food and Drug Administration: a federal agency in the Department of Health and Human Services established to regulate the release of new medical products and, finally, if required by an established review body of the participating hospitals or institutions. The female donor is informed that she will be subject to risk assessment to determine if she is qualified as an amniotic fluid donor. She will also be informed of the tests for the risk assessment. The female donor is further informed that, if she is selected as an amniotic fluid donor based on the risk assessment, her birth tissues, such as placenta and amniotic fluid, may be collected at birth, tested and processed for medical uses. The informed consent includes consent for risk assessment and consent for donation of birth tissues and amniotic fluid.

Risk assessment is conducted on the female donor with informed consent to evaluate her risk factors for communicable diseases, such as human immunodeficiency virus (HIV), hepatitis B virus (HBV), hepatitis C virus (HCV), cytomegalovirus (CMV), human T-lymphotropic virus (HTLV), syphilis, etc., as is required by regulating bodies. Medical and social histories of the female donor, including physical exam record, and/or risk assessment questionnaire, are reviewed. Those with high risk factors for the communicable diseases are excluded.

Consent to draw blood at the time of delivery and 1 to 12 months post-delivery is obtained from female donors with low risk factors for the communicable diseases. Screening tests on communicable diseases, such as HIV 1 and 2, HCV, HbCore, syphilis, HTLV I/II, CMV, hepatitis B and C, are conducted by conventional serological tests on the blood sample obtained at birth. The initial screening tests are preferably completed within 7 days after birth. Preferably, the screening tests are conducted again on a second blood sample collected a few months post-delivery, to verify the previous screening results and to allow for detection of communicable disease acquired shortly before birth, but are shown as "negative" on the previous screening tests. The second blood sample can be collected 1-12 months, preferably 6 months, post birth.

Only female donors with informed consent who are tested negative for the communicable diseases are approved as amniotic fluid donors. In a preferred embodiment, only female donors with informed consent who are tested negative for the communicable diseases in both screening tests with the blood sample drawn at birth and the blood sample drawn 6 months post-delivery are approved as amniotic fluid donors.

In order for a wound to heal, extracellular matrix need not only be laid down over the wound, but the extracellular matrix must also undergo degradation and remodeling to form a mature tissue. Proteases, particularly matrix metalloproteinases (MMPs), are known to degrade extracellular matrix components, and during normal wound healing, MMP activity is appropriately balanced by endogenous protease inhibitors. In contrast, in chronic wounds, the balance between MMP and the activity of endogenous protease inhibitors is disturbed, which can result in an increased activity or concentration of MMPs. Accordingly, and without wishing to be bound by any theories, it is believed that the high concentration of TIMPs in amniotic fluid near term can inhibit the activity of proteases having elevated activity in chronic wounds, particularly MMPs, thereby facilitating the healing of chronic wounds.

The following examples of the present invention are to further illustrate the nature of the invention. It should be understood that the following examples do not limit the invention and that the scope of the invention is to be determined by the appended claims.

EXAMPLES

Example 1

Treatment of a Chronic Wound with Human Amniotic Fluid Comprising TIMPs

Amniotic fluid is isolated from a pregnant human female donor undergoing a pre-term Caesarean section delivery at week 36 of gestation. The isolated amniotic fluid is processed by concentrating the fluid to remove excess water, thus increasing the effective concentration of endogenous TIMPs in the amniotic fluid.

The processed amniotic fluid is applied directly to a human patient having a chronic leg ulcer. The processed human amniotic fluid is applied at least once per day. Healing of the ulcer is monitored at least by observing the boundaries of the wound. The processed human amniotic fluid is continually applied to the ulcer at least once a day until the ulcer is healed.

Example 2

Treatment of a Chronic wound with Human Amniotic Fluid Comprising TIMPs

Amniotic fluid is isolated from a pregnant human female donor undergoing a pre-term Caesarean section delivery at week 36 of gestation. The isolated amniotic fluid is processed by concentrating the fluid to remove excess water, thus increasing the effective concentration of endogenous TIMPs in the amniotic fluid. Purified TIMPs are added to the processed amniotic fluid to further increase the concentration of TIMPs.

The processed amniotic fluid is applied directly to a human patient having a chronic leg ulcer. The processed human amniotic fluid is applied at least once per day. Healing of the ulcer is monitored by observing the boundaries of the wound. The processed human amniotic fluid is continually applied at least once a day until the ulcer is healed.

Example 3

Treatment of a Chronic Wound with Human Amniotic Fluid Comprising TIMPs

Amniotic fluid is isolated from a pregnant human female donor undergoing a pre-term Caesarean section delivery at week 36 of gestation. The isolated amniotic fluid is processed by concentrating the fluid to remove excess water, thus increasing the effective concentration of endogenous TIMPs in the amniotic fluid.

A leg ulcer in a patient is identified as a chronic wound having elevated protease activity by using a commercially available kit that measures MMP activity according to the manufacturer's instructions. The processed amniotic fluid is applied to the leg ulcer at least once a day until the ulcer is healed.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCES (1) Trengrove et al. Analysis of the acute and chronic wound environments: the role of proteases and their inhibitors. *Wound Repair and Regeneration,* (1999) 7, 442-452.

(2) Serena et al. Protease Activity Levels Associated with Healing Status of Chronic Wounds (2012) EP429 *European Wound Management Association* (poster abstract).

(3) Wysocki et al. Wound Fluid from Chronic Leg Ulcers Contains Elevated Levels of metalloproteinases MMP-2 and MMP-9. *Journal of Investigative Dermatology,* (1993) 1(1), 64-68.

(4) Snyder et al. Point of Care Diagnostic Tests in Wound Management; Targeted Therapy for Excessive Protease Activity-the First Frontier. *Wound Care & Hyperbaric Medicine,* (2011) 2(3).

(5) Trelford et al. The amnion in surgery, past and present. *Am J Obstet Gynecol.* (1979) 134(7): 833-45.

(6) Niknejad et al. Properties of the amniotic membrane for potential use in tissue engineering. *Eur Cell Mater.* (2008) 15, 88-99.

(7) Weiss et al. The matrix metalloproteinases (MMPs) in the decidua and fetal membranes. *Frontiers in Bioscience* (2007) 12, 649-59.

(8) Riley et al. Secretion of tissue inhibitors of matrix metalloproteinases by human fetal membranes, decidua, and placenta at parturition. *J. Endocrinology* (1999) 162, 351-59.

(9) Maymon et al. A role for the 72 kDa gelatinase (MMP-2) and its inhibitor (TIMP-2) in human parturition, premature rupture of membranes and intraamniotic infection. *J. Perinatal Medicine* (2005) 29(4), 308-316.

(10) Athayde et al. Matrix metalloproteinases-9 in preterm and term human parturition. *J. Matern. Fetal Med.* (1999) 8(5), 213-9.

(11) Menon et al. The role of matrix degrading enzymes and apoptosis in rupture of membranes. *J. Soc. Gynecol. Investig.* (2004) 11(7), 427-37.

(12) McLaren et al. Increased concentration of pro-matrix metalloproteinase 9 in term fetal membranes overlying the cervix before labor: implications for membrane remodeling and rupture.

(13) Athayde et al. A role for matrix metalloproteinase-9 in spontaneous rupture of the fetal membranes. *Am. J. Obstet. Gynecol.* (1998) 179(5), 1248-53.

(14) Pasquier et al. Fetal membranes: embryological development, structure and the physiopathology of the pre-term premature rupture of membranes. *J. Gynecol. Obstet. Biol. Reprod. (Paris)* (2008) 37(6), 579-88.

(15) Moore et al. The physiology of fetal membrane rupture: insight gained from the determination of physical properties. *Placenta* (2006) 27(11-12) 1037-51.

(16) Park et al. Role of cytokines in preterm labor and birth. *Minerva Ginecol.* (2005) 57(4), 349-66.

(17) Wang et al. Role of matrix metalloproteinases-2,9 and their inhibitors in premature rupture of membranes. *Zhonghua Fu Chan Ke Za Zhi* (2005) 40(1) 29-33.

(18) Lu et al. Clinical significance of matrix metalloproteinase-9/tissue inhibitors of matrix metalloproteinase-1 imbalance in maternal serum, amniotic fluid, umbilical cord serum in patients with premature rupture of the membranes.

(19) Vadillo-Ortega et al. 92-kd type IV collagenase (matrix metalloproteinase-9) activity in human amniochorion increases with labor. *Am. J. Pathol.* (1995) 146(1), 148-56.

(20) Gordon et al. Metalloproteinase inhibitors as therapeutics. *Clin. Exp. Rheumatol.* (1993) Suppl. 8: S91-4.

(21) Fortunato et al. Presence of four tissue inhibitors of matrix metalloproteinases (TIMP-1, -2, -3, and -4) in human fetal membranes. *Am. J. Reprod. Immunol.* (1998) 40(6), 395-400.

(22) Fortunato et al. Collagenolytic enzymes (gelatinases) and their inhibitors in human amniochorionic membrane. *Am. J. Obstet. Gynecol.* (1997) 177(4), 731-41.

(23) Vadillo-Ortego et al. Increased matrix metalloproteinase activity and reduced tissue inhibitor of metalloproteinases-1 levels in amniotic fluids from pregnancies complicated by premature rupture of membranes. *Am. J. Obstet. Gynecol.* (1996) 174(4), 1371.

(24) Hampson et al. Amniotic membrane collagen content and type distribution in women with preterm premature rupture of the membranes in pregnancy. *Br. J. Obstet. Gynecol.* (1997) 104(9), 1087.

(25) Bryant-Greenwood et al. Control of peripartal collagenolysis in the human chorion-decidua. *Am. J. Obstet. Gynecol.* (1995) 172 (1 Pt 1): 63.

(26) Draper et al. Elevated protease activities in human amnion and chorion correlate with preterm premature rupture of membranes. *Am. J. Obstet. Gynecol.* (1995) 173(5) 1506.

(27) Lei et al. 92 kDa gelatinase (matrix metalloproteinase-9) is induced in rat amnion immediately prior to parturition. *Biol. Reprod.* (1995) 53(2): 339.

I claim:

1. A method of treating a chronic wound in a subject in need thereof, wherein the chronic wound has elevated protease activity, the method comprising:
   (1) identifying a chronic wound as having elevated protease activity; and
   (2) applying an effective amount of human amniotic fluid comprising a therapeutically effective amount of tissue inhibitors of matrix metalloproteinases to the chronic wound identified as having elevated protease activity, thereby treating the chronic wound,
   wherein the human amniotic fluid is free of cellular debris.

2. The method according to claim 1, wherein the amniotic fluid is obtained from a female donor between week 28 and week 37 of pregnancy.

3. The method according to claim 1, wherein the step of identifying the chronic wound as having elevated protease activity comprises detecting activity or concentration of one or more matrix metalloproteinases (MMPs) in the wound.

4. The method according to claim 3, wherein the one or more MMPs is selected from the group consisting of MMP-1, MMP-2, MMP-8, and MMP-9.

5. The method according to claim 1, wherein the chronic wound is selected from the group consisting of a non-healing surgical wound, burn, trauma wound, or amputation wound, and a failed skin graft.

6. The method according to claim 1, wherein the chronic wound is an ulcer selected from the group consisting of diabetic ulcer, diabetic foot ulcer, venous ulcer, venous leg ulcer, and decubitus (pressure) ulcer.

7. The method according to claim 1, wherein the amniotic fluid is administered in combination with one or more active agents selected from the group consisting of morphogenic proteins, small molecule compounds, pharmaceutical agents, anti-microbial agents, anti-inflammatory agent, agents that prevent scarring and/or adhesions, and analgesics.

8. The method according to claim 1, wherein the amniotic fluid is supplemented with exogenously added TIMPs.

9. A method of treating a chronic wound in a subject in need thereof, comprising:
(1) applying a wound dressing to the chronic wound, said wound dressing comprising an effective amount of human amniotic fluid, said human amniotic fluid comprising a therapeutically effective amount of tissue inhibitors of matrix metalloproteinases (TIMPs) and being free of cellular debris; and
(2) optionally identifying the chronic wound as having elevated protease activity prior to applying the wound dressing,
thereby treating the chronic wound.

10. The method of claim 1, wherein a concentration of the tissue inhibitors of matrix metalloproteinases in the human amniotic fluid is determined prior to applying the human amniotic fluid to the chronic wound.

11. The method claim 10, including verifying that the human amniotic fluid includes the therapeutically effective amount of tissue inhibitors of matrix metalloproteinases by determining the concentration of the tissue inhibitors of matrix metalloproteinases in the human amniotic fluid prior to applying the human amniotic fluid to the chronic wound.

12. The method of claim 11, including processing the human amniotic fluid when the human amniotic fluid does not include the therapeutically effective amount of tissue inhibitors of matrix metalloproteinases.

13. The method of claim 12, wherein processing the human amniotic fluid includes removing water from the human amniotic fluid.

14. The method of claim 12, wherein processing the human amniotic fluid includes increasing the concentration of the tissue inhibitors of matrix metalloproteinases in the human amniotic fluid.

* * * * *